(12) United States Patent
Messier

(10) Patent No.: US 7,955,997 B2
(45) Date of Patent: Jun. 7, 2011

(54) ELECTROSTATICALLY CHARGED FILTER MEDIA INCORPORATING AN ACTIVE AGENT

(75) Inventor: Pierre Jean Messier, Mirabel (CA)

(73) Assignee: Triosyn Corp., Williston, VT (US)

(*) Notice: Subject to any disclaimer, the term of this patent is extended or adjusted under 35 U.S.C. 154(b) by 425 days.

(21) Appl. No.: 10/528,005

(22) PCT Filed: Sep. 8, 2003

(86) PCT No.: PCT/IB03/04553
§ 371 (c)(1),
(2), (4) Date: Jun. 9, 2006

(87) PCT Pub. No.: WO2004/024278
PCT Pub. Date: Mar. 25, 2004

(65) Prior Publication Data
US 2006/0251879 A1   Nov. 9, 2006

Related U.S. Application Data

(60) Provisional application No. 60/411,006, filed on Sep. 16, 2002, provisional application No. 60/434,526, filed on Dec. 19, 2002, provisional application No. 60/458,800, filed on Mar. 28, 2003.

(51) Int. Cl.
*B32B 5/16* (2006.01)
*A61K 31/74* (2006.01)

(52) U.S. Cl. ..... 442/417; 442/327; 442/414; 424/78.08; 424/78.1

(58) Field of Classification Search ............ 442/327, 442/375, 414, 417; 424/78.08, 78.1; 210/263, 210/48, 491, 507, 508
See application file for complete search history.

(56) References Cited

U.S. PATENT DOCUMENTS

| | | | |
|---|---|---|---|
| 2,765,788 A | 10/1956 | Raiche |
| 3,971,373 A | 7/1976 | Braun |
| 4,033,125 A | 7/1977 | Inada et al. |
| 4,100,324 A | 7/1978 | Anderson et al. |
| 4,215,682 A | 8/1980 | Kubik et al. |
| 4,323,063 A | 4/1982 | Fisichella |
| 4,626,263 A | 12/1986 | Inoue et al. |
| 4,784,909 A | 11/1988 | Emi et al. |
| 4,797,318 A | 1/1989 | Brooker et al. |
| 4,865,755 A | 9/1989 | Lloyd |
| 4,917,942 A | 4/1990 | Winters |
| 4,927,692 A | 5/1990 | Dhanakoti et al. |
| 4,951,664 A | 8/1990 | Niemeyer |
| 5,112,677 A | 5/1992 | Tani et al. |
| 5,209,563 A | 5/1993 | Swisher, Jr. et al. |
| 5,409,766 A | 4/1995 | Yuasa et al. |
| 5,411,576 A | 5/1995 | Jones et al. |

(Continued)

FOREIGN PATENT DOCUMENTS

CA   1243801   11/1988

(Continued)

*Primary Examiner* — Angela Ortiz
*Assistant Examiner* — Jennifer Steele
(74) *Attorney, Agent, or Firm* — Goodwin Procter LLP

(57) ABSTRACT

There is provided a protective media and a method of manufacturing the same. In one aspect, the protective media includes a porous dielectric carrier, an active agent incorporated in the porous dielectric carrier, and an electrostatic charge across at least a portion of the porous dielectric carrier. This innovative media is capable of eradicating microorganisms and/or toxins more efficiently than prior art solutions and can also self sterilize.

17 Claims, 4 Drawing Sheets

U.S. PATENT DOCUMENTS

| | | | |
|---|---|---|---|
| 5,419,794 A | 5/1995 | Hauber et al. | |
| 5,472,481 A | 12/1995 | Jones et al. | |
| 5,503,745 A | 4/1996 | Ogata et al. | |
| 5,556,618 A * | 9/1996 | Ando et al. | 424/78.08 |
| 5,582,865 A | 12/1996 | Rezuke et al. | |
| 5,639,452 A * | 6/1997 | Messier | 424/78.1 |
| 5,641,555 A | 6/1997 | Berrigan et al. | |
| 5,645,057 A | 7/1997 | Watt et al. | |
| 5,747,053 A | 5/1998 | Nashimoto et al. | |
| 5,873,968 A * | 2/1999 | Pike et al. | 156/73.2 |
| 5,908,598 A | 6/1999 | Rousseau et al. | |
| 5,980,827 A | 11/1999 | Messier | |
| 6,045,820 A | 4/2000 | Messier | |
| 6,119,691 A | 9/2000 | Angadjivand et al. | |
| 6,224,655 B1 * | 5/2001 | Messier | 96/226 |
| 6,234,171 B1 | 5/2001 | Springett et al. | |
| 6,419,871 B1 | 7/2002 | Ogale | |
| 6,453,544 B2 | 9/2002 | Cioletti et al. | |
| 6,565,866 B2 | 5/2003 | Gottlund et al. | |
| 6,592,861 B2 | 7/2003 | Messier | |
| 6,627,563 B1 | 9/2003 | Huberty | |
| 6,680,050 B1 | 1/2004 | Messier | |
| 6,696,055 B2 | 2/2004 | Messier | |
| 6,838,186 B2 | 1/2005 | Aral et al. | |
| 6,841,791 B2 | 1/2005 | DeMeo et al. | |
| 6,872,241 B2 | 3/2005 | Soane et al. | |
| 6,899,868 B2 | 5/2005 | Messier | |
| 6,946,196 B2 | 9/2005 | Foss | |
| 2001/0004361 A1 | 6/2001 | Kobayashi | |
| 2001/0009661 A1 | 7/2001 | Messier | |
| 2001/0042361 A1 | 11/2001 | Cox et al. | |
| 2001/0045398 A1 | 11/2001 | Messier | |
| 2002/0150623 A1 | 10/2002 | Messier | |
| 2003/0099606 A1 | 5/2003 | Messier | |
| 2006/0144406 A1 | 7/2006 | Niolchev et al. | |

FOREIGN PATENT DOCUMENTS

| | | |
|---|---|---|
| DE | 2929956 | 2/1981 |
| DE | 38 39 956 | 6/1989 |
| EP | 0241221 | 10/1987 |
| FR | 1 348 800 | 1/1964 |
| GB | 2077112 | 12/1981 |
| JP | 62-074423 | 4/1987 |
| JP | 05-031269 | 2/1993 |
| JP | 08-284063 | 10/1996 |
| JP | 10-141757 | 5/1998 |
| JP | 2001-314491 | 11/2001 |
| WO | WO 96/37292 | 11/1996 |
| WO | WO 00/01737 | 1/2000 |
| WO | WO01/14042 | 1/2001 |
| WO | WO 01/14042 | 3/2001 |
| WO | WO 01/55494 | 8/2001 |
| WO | WO 02/076576 | 10/2002 |
| WO | WO02076576 | 10/2002 |
| WO | WO2006/037929 | 4/2006 |

* cited by examiner

SINGLE MEDIA

ELECTROSTATICALLY CHARGED FILTER MEDIA INCORPORATING AN ACTIVE AGENT

CROSS-REFERENCE TO RELATED APPLICATIONS

This application claims the benefit of priority to U.S. Provisional Application Nos. 60/411,006, 60/434,526 and 60/458,800, filed on Sep. 16, 2002, Dec. 19, 2002 and Mar. 28, 2003, respectively, the contents of each are hereby incorporated by reference herein in the entirety.

STATEMENT REGARDING FEDERALLY SPONSORED RESEARCH OR DEVELOPMENT

Not applicable.

REFERENCES TO SEQUENCE LISTING, TABLES OR COMPUTER PROGRAM LISTING APPENDIX ON COMPACT DISK

Not applicable.

FIELD OF THE INVENTION

The present invention relates to electrostatically charged filter media and more particularly to an electrostatically charged media with an active agent incorporated thereon, and a method of making the same.

BACKGROUND OF THE INVENTION

Prior art filter methods include, for example, mechanical filtration—a physical retention of particles larger than the pores of the filter media; electrostatic filtration—adhering particles to fibers in the filter without killing/deactivating the particles; and filtration as taught and claimed in U.S. Pat. No. 5,980,827 which issued to the inventor hereof on Nov. 9, 1999 and is entitled “Disinfection Of Air Using An Iodine/Resin Disinfectant.” It has been determined that improved iodinated resin filtration occurs in a thin media when the product is incorporated to a media with a convoluted pathway. By forcing the microorganism/toxin to pass through a circuitous route, the microorganism/toxin is eventually killed/deactivated. One method for providing a circuitous route is to employ a nonwoven media.

In published U.S. patent application number 20010045398 entitled “Process For The Immobilisation Of Particles In A Three Dimensional Matrix Structure” the non-woven material is first produced and then an iodinated resin, such as the one disclosed in U.S. Pat. No. 5,639,452 (the ’452 patent) is added using alcohol or a partial solvent with a high pulsation vacuum pump that opens the filter pores so that the active agent will go through it (the “Triosyn” resin). The contents of the ’452 patent is incorporated by reference in its entirety herein.

U.S. Pat. No. 6,346,125 teaches incorporating an aqueous antimicrobial agent into a non-electrostatically charged non-woven material. Specifically, the ’125 patent describes a particular process for incorporating an aqueous antimicrobial agent into a non-electrostatically charged non-woven. However, without the electrostatic properties, the non-woven must be of greater thickness so that the microorganism has sufficient contact time with the antimicrobial agent for decontamination.

U.S. Pat. No. 5,952,092 teaches a non-woven fabric with chemically active particles. However, this patent does not teach using an electrostatic substrate as in the present innovation.

Nonwoven electrets and methods of manufacturing the same are known in the art. For example, U.S. Pat. No. 5,409,766 describes a nonwoven fabric in an electret state composed of monofilaments formed of a polymer composition capable of dust collection over a prolonged time and in a hot and humid condition. Also disclosed are processes for producing this nonwoven fabric, as well as a filtering air masking material composed of that nonwoven fabric. However, this prior art system does not provide antimicrobial/antitoxin properties. Thus, the microorganism/toxin, while suspended within the nonwoven fabric, is not sterilized or deactivated. Once the electrostatic properties of the nonwoven are depleted or the material is saturated, the microorganism/toxin may be released back into the atmosphere.

Electrostatically charged filters are known to be used in facemasks, for example. With respect to both, one of the problems of face seal is well known and represents a limitation that the industry has been trying to address. The problem resides in the fact that from one morphological physical structure of a human being or structure to the next the differences generate such a wide spectrum of geometrical deviations that it has been difficult to create a 100% airtight seal. For a facemask the difficulty in creating a seal occurs between the skin and the mask for a range of face sizes and shapes. Various different technological means have been tried, for example using, adhesive seals, flat and wide seals and resilient material seals. The industry has oriented its work on creating an airtight seal, however, the pressure differential generated actually forces air in the gaps between seal and skin thus bypassing the air filter material. The electrostatic filter of the present invention may be made of a spongy or other breathable nonwoven material so as to minimize the pressure differential, thus preventing air from being forced through the gaps. Further, it effectively makes the gasket used to create a closure between the user and the facemask out of a thin filter having a low-pressure drop like the electrostatic filter and having the added benefit of the active agent incorporated thereon.

Other known prior art that teach the use of high pressure drop media includes the mechanical filtration of the HEPA filter. However, the pressure drop of the present invention is approximately 50% to 90% lower than that of the HEPA filter alone. The filter further includes a material that kills on passage vegetative bacteria, spores, and viruses. They are filtered out of the airstream and are killed. In addition, the present invention is self-sterilizing, meaning that not only does it filter air passed there through, it kills the bacteria trapped on the filter. Therefore, the media protects both the user and the outside air.

Given the shortcomings of the prior art, it is advantageous to have an electret, which has improved characteristics over known solutions. The present innovation comprises a substrate that supports an active agent and is a dielectric.

SUMMARY OF THE INVENTION

The present invention overcomes the aforementioned problems of the prior art. Specifically and in accordance with one aspect of the present invention, there is provided herein an electrostatically charged non-woven media that has active agents incorporated therein. This innovative media is capable of eradicating microorganisms and/or toxins more efficiently than prior art solutions and can also self-sterilize.

The present invention additionally provides for methods of making the electrostatically charged filter media having an active agent incorporated therein. The substrate may be manufactured according to various methods; the active agent may be incorporated according to various methods; and the electrostatic charge may be provided according to various methods, all of which are described herein or are known in the art.

Because substantially less active agent is used for each filter costs are reduced while maintaining effectiveness. Additionally, the enhanced electrostatic filter of the present invention provides added performance of the active agent and electrostatic properties.

In addition to the above aspects of the present invention, additional aspects, features and advantages will become better understood with regard to the following description in connection with the accompanying drawings.

DETAILED DESCRIPTION OF THE INVENTION

The following sections describe exemplary embodiments of the present invention. It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto.

The present invention provides an electrostatically charged filter media comprising a substrate with an active agent incorporated therein.

Filter Media

The filter media of the present invention includes (1) a substrate, (2) an active agent incorporated therein and (3) an electrostatic charge.

Substrate

The substrate comprises any material having dielectric properties or capable of being enhanced to have dielectric properties and which is capable of having an active agent incorporated therein.

In a particular embodiment, the substrate may be a fiber based material having a fibrous matrix structure; it may be a sponge like material have an open cell matrix structure; it may be flexible or inflexible; etc.

Figure 1:
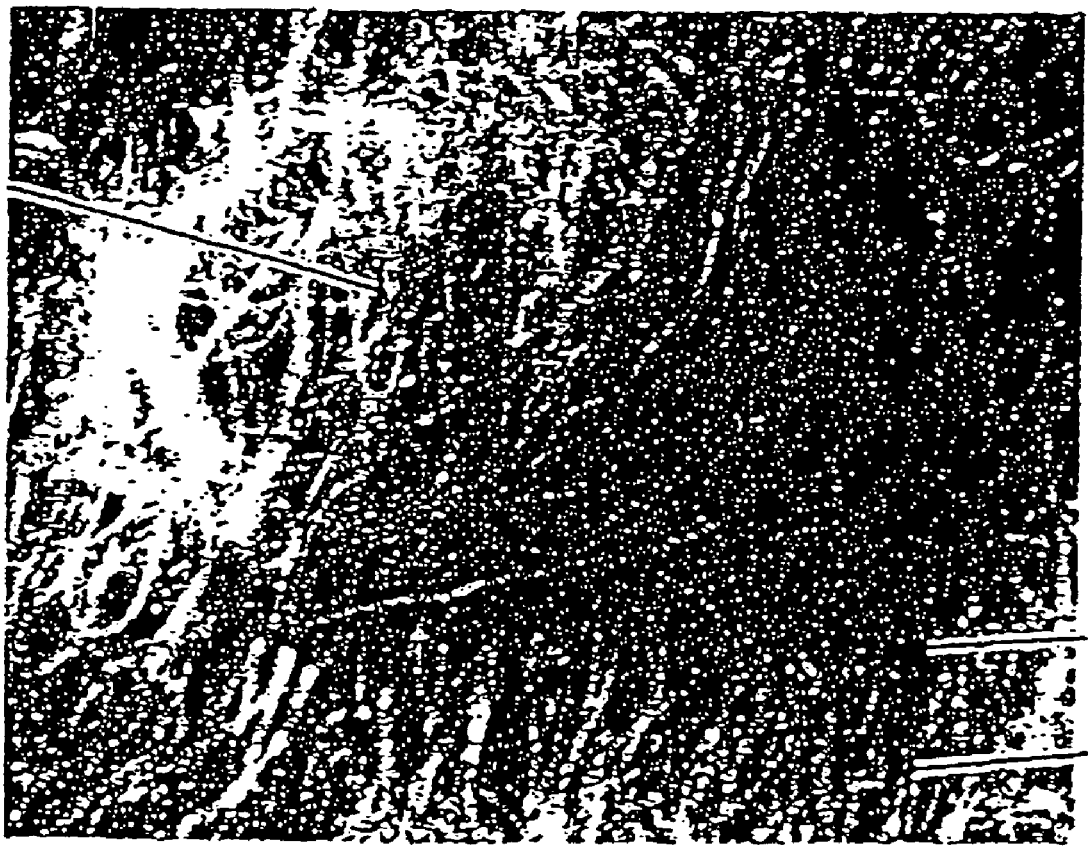
FIG. 1 depicts aspects of an exemplary embodiment of the present invention in accordance with the teachings presented herein.

As stated above, in one embodiment, the substrate is a nonwoven fabric. Nonwoven is a type of fabric that is bonded together rather than being spun and woven into a cloth. It may be a manufactured sheet, mat, web or batt of directionally or randomly oriented fibers bonded by friction or adhesion; it may take the form of a type of fabric. FIG. 1 is provided as an exemplary embodiment of a nonwoven fabric.

In another embodiment, the substrate may be a nonwoven textile of varying fluffiness, comprising polymer fiber. The polymer may be for example, nylon, polyethylene, polypropylene, polyester, etc. or any other polymer suitable for a filter substrate. Additionally, the substrate can be made of materials other than polymer fiber.

The nonwoven material may be of a type suitable for a high efficiency particulate air filter (i.e. a HEPA filter). A suitable nonwoven material may be obtained from Technol Aix en Provence Cedex 03 France (see Canadian patent no. 1,243,801); another suitable material may also be obtained from Minnesota Mining & Manufacturing Co. (3M). The nonwoven material has a three dimensional structure which should be configured in such a fashion as to provide a matrix capable to entrap (i.e. physically) the desired active agent. For example if the nonwoven material is based on fibers, the structural fibers of the nonwoven material may be present and distributed in such a fashion as to provide a fibrous matrix structure able to entrap the desired active agent. The nonwoven material may have a microstructure. In a particular embodiment, the active agent has a size appropriate to be entrapped by the three dimensional (e.g. web) matrix structure of the desired nonwoven material.

Alternative substrates may further include glass fibers and fibers, such as cellulose, that are ultimately formed into a paper-based filter media. Any substrate capable of acting as carrier for the active agent and having dielectric properties or capable of having dielectric properties imparted to it, would be a suitable substrate for the present invention. When substrates that do not have strong dielectric properties are used, such as glass fibers, additives may be provided to improve the dielectric properties of the substrate. The present invention is not limited to a nonwoven material. Other suitable substrates may include spongy materials or foam.

Active Agent

The active agent of the present invention may be, for example, an antimicrobial, an antitoxin, or the like. The antimicrobial may be biostatic and/or biocidal. Biostatic is a material that inhibits the growth of all or some of bacteria spores, viruses, fungi, etc. (having bioactive particles), and a biocidal is a material that kills all or some of bacteria spores, viruses, fungi, etc. Preferably, the biocidal comprises the iodinated resin particles, such as those described above in the '452 patent, as described above. Other suitable active agents include silver, copper, zeolyte with an antimicrobial attached thereto, halogenated resins, and agents capable of devitalizing/deactivating microorganisms/toxins that are known in the art, including for example activated carbon, other metals and other chemical compounds. For example, a non-exhaustive list of suitable metals and/or chemical compounds is as follows:

Exemplary Metals
Aluminum
Barium
Boron
Calcium
Chromium
Copper
Iron
Magnesium
Manganese
Molybdenum
Nickel
Lead
Potassium
Silicon
Sodium
Strontium
Zinc
Exemplary Chemical Compounds N-methyl piperazine
Potassium Hydroxide
Zinc Chloride
Calcium chloride
Mixture of Sodium carbonate and sodium bicarbonate Reference in the specification to antimicrobial is used for ease of reading and is not meant to be limiting.

Electrostatic Charge

The filter media with an active agent incorporated thereon is also electrostatically charged. Accordingly, there is a potential across the surface(s) of the media creating a field wherein the field can attract and/or repel charged particles introduced to the media so that in some instances it alters the path of travel of the charged particles.

Figure 2:
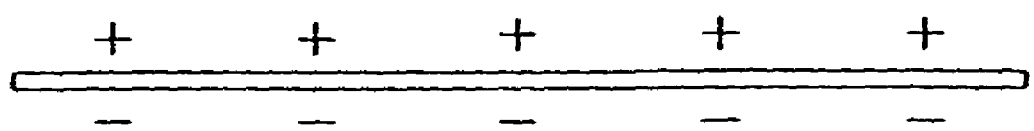
FIGS. 2 and 3 depict exemplary embodiments of electrostatically charged substrates.
Figure 3:
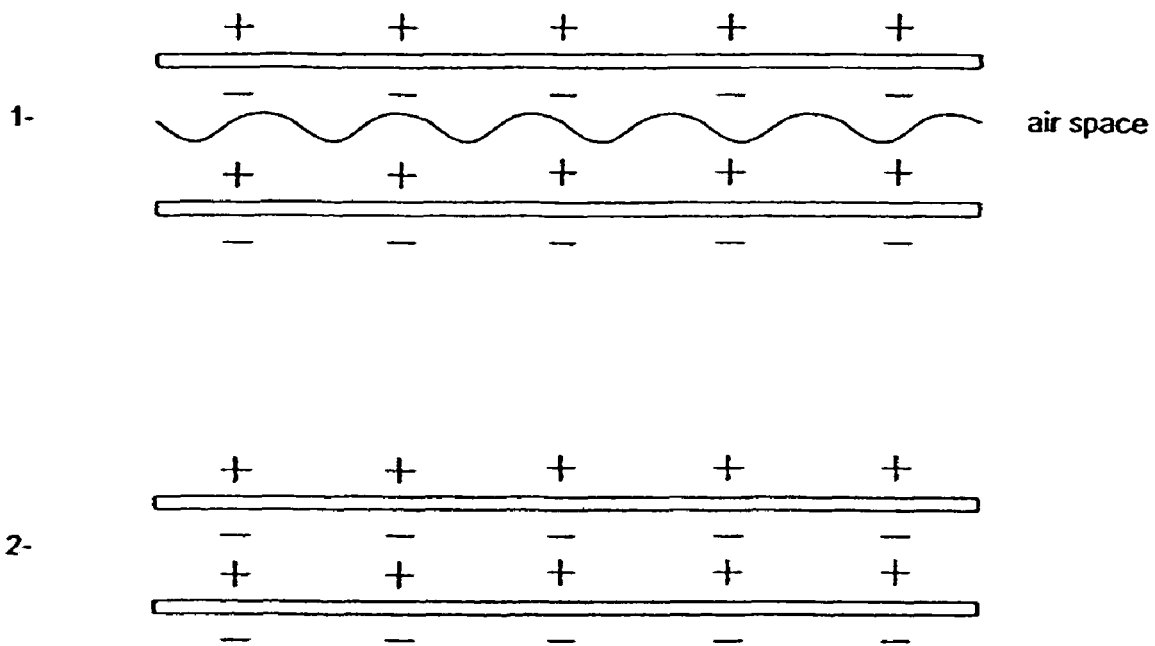

FIGS. 2-3 provide exemplary representations of electrostatically charged media. Electrostatically charged filter media of the present invention may, for example, be single or multi-layered. Each layer may be individually charged. A single layered media can have a positive charge on one side and a negative charge on the other. An example of a multi-layered media is a double-layered media. Preferably, a double layered media is used wherein the double-layered media comprises two layers, each being positively charged on one side and negatively charge on the other side, wherein the two layers are separated by an airspace and the two layers are oriented so that the negative side of one of the two layers is closest to the positive side of the other layer. In this two-layer embodiment, the air space increases the net dielectric constant of the electrostatically charged filter media.

Preferably, a high dielectric constant is provided to maintain the charge for an extended period of time. For example, air provides a good dielectric constant, as can be employed in an airspace as described above. Thus, the present invention may be effective even when wet or in a humid environment.

The resulting media is an insulating carrier with an active agent adhered thereto or impregnated therein and having an electrostatic charge. The media according to the present invention can be produced of different thickness, density and pressure drop. The media described herein can be used in, for example: clothing, wound dressings, air filters, shelters, liners and generally, any filter material.

Method of Manufacturing

The present invention additionally provides for a method of manufacturing the electrostatically charged filter media having an active agent incorporated thereon. The substrate itself may be manufactured according to various known methods, such as melt blown, spun blown, air laid, carted, etc.

Method of Incorporating the Active Agent

Prior art incorporation methods using polypropylene require the use of polyethylene to maintain a tackiness to the fibers to hold the solid particulate for a longer amount of time to prevent the particulate from falling off the fibers. In the present invention, the active agent, such as the iodinated resin disclosed in the '452 patent, may be physically entrapped in the fibers. Thus, the active agent does not have to adhere to the fibers to be incorporated into the media.

In the present invention, the active agent may be incorporated to the substrate according to various methods. For example, liquid emulsification of the active agent in the melt at increased temperature and increased pressure for mix and melt processes, or incorporation by spraying the active agent after extrusion of non-woven fibers during processing.

Figure 4:
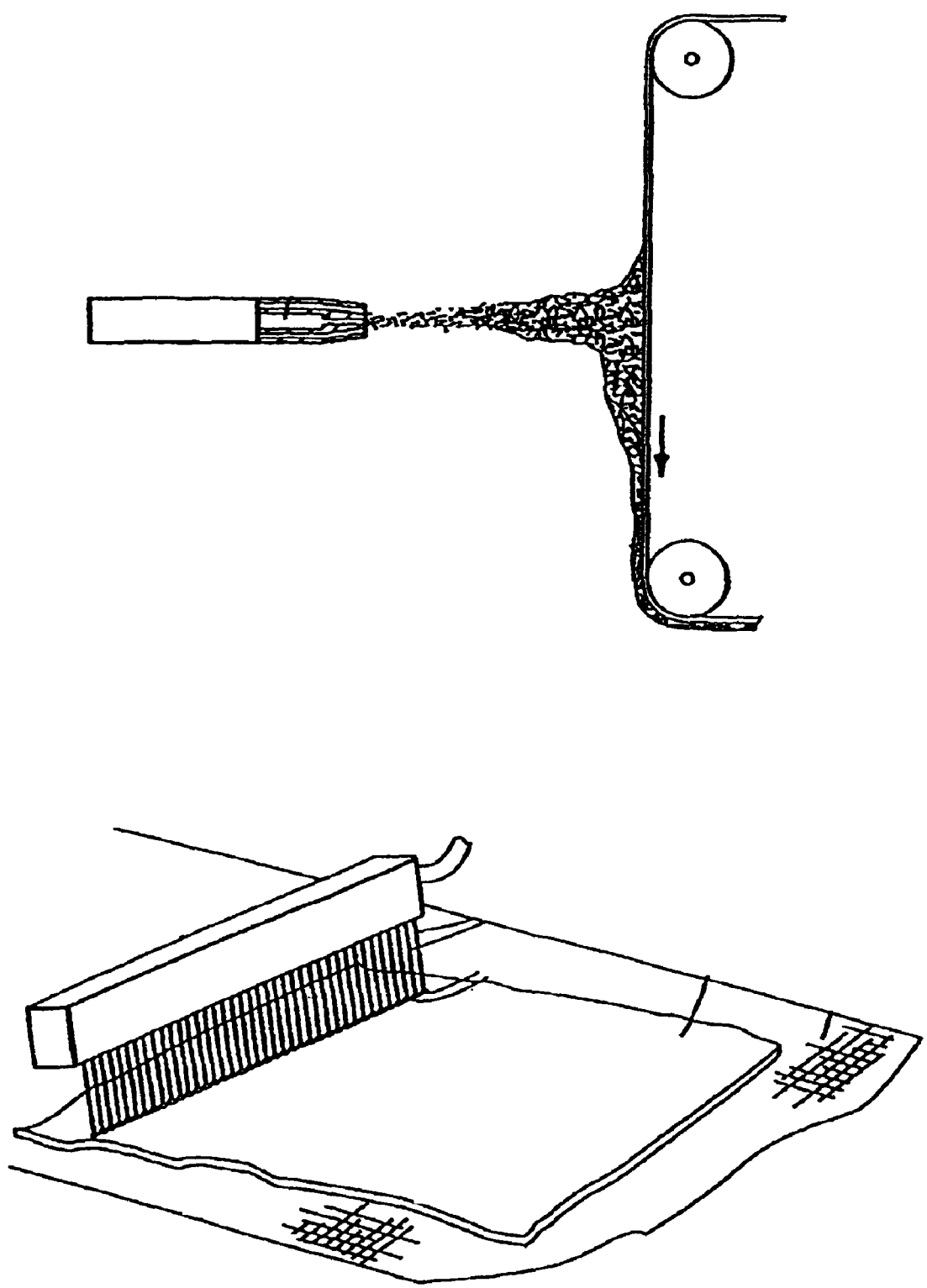
FIG. 4 depicts an exemplary embodiment for providing a nonwoven media with an active agent incorporated thereon.

In a preferred embodiment, as shown in FIG. 4, polymer granules, such as polypropylene granules, are extruded through an extruder; the extruded fibers being of varying thickness and length. As the fibers are extruded they fall toward a collecting web. A desired active agent is provided in a cloud at a location closest to the extrusion point of the resulting fibers. The cloud envelops the cooling fibers while the fibers are still in a quasi-liquid quasi-solid state. In one embodiment, the active agent particulate may range from 0.2 microns to 0.5 millimeters. However, one of ordinary skill in the art can apply active agents with smaller and bigger particulates size. The active agent particulate settles and collects so that it is intermeshed or entrapped with the fibers on the collecting web. After the fibers with the active agent incorporated thereon falls to the collecting web, the resulting media is formed into a mesh by known methods. Additionally, the cloud may be in various physical states including a vapor, fine dry dust, or atomized or aerosolized particulate. Advantageously, cloud incorporation may occur at room temperature with particulate also at room temperature. Further, the thickness, length and pressure define the mechanical properties of the resulting media.

A suitable melt blown system for the above embodiment is the Accuweb provided by Accurate Products Co. of Hillside, N.J.

Various other methods of incorporating an active agent to a filter media are suitable for the present invention. First, for example, using the method disclosed in published U.S patent application number 20010045398 A1. Second, soaking a bail of hair-like extruded fibers in an active agent (and using alcohol to achieve the soak) and then creating the felt using pressure and temperature. Third, taking solid polymer granules manufactured with an active agent mixed in an extruder hopper to create a mixture that is then extruded into fine hair-like bails. Felt is then formed through a temperature and pressure process. Fourth, extruding a substrate, such as a polymer in to a hair-like substance on to which an active agent is sprayed in solid after the extrusion. The active agent may be vaporized like an aerosol. Fifth, the active agent can be injected or sprayed into non-woven fabric as the fabric is being pressurized. Sixth, carting bails of filament and mixing the resulting media with the active agent to generate a sheet having the active agent incorporated therein. Seventh, depositing the active agent on a non-woven media and thereafter needle-punching the media to impregnate the active agent through and through the media. Other methods may be used.

In another embodiment of the present invention, polymer granules are placed in a hopper of an extruder with active agent in dust form prior to extrusion. Thus, the active agent is mixed in the hopper prior to the melt. The two components are mixed, heated and then extruded to form a thin "hair" fiber used to make a felt. The resulting hair in the above embodiments having the active agent incorporated thereto is a bail-like wool. The substrate could be transparent depending on the polymer used. Additionally, a resulting polymer fiber having the active agent incorporated thereto can be treated with water, pressurized and then heated to form a felt. In other embodiments, the resulting polymer fiber having the active agent incorporated thereto can an be air laid, vacuum laid, water laid, etc.

Although not specifically described herein, other conventional or known methods that achieve incorporation of an active agent to a substrate are suitable for the present invention. Thus, at this point the substrate has an active agent incorporated therein.

Method of Electrostatically Charging

The substrate having an active agent incorporated therein is provided with an electrostatic charge. The charge may be induced by using a corona, needle punching, chemical enhancement, any other known charge inducing system or method, or a combination of any of the foregoing. Needle punching creates high-level friction thus adding a charge.

In a particular embodiment, to make the electrostatically charged non-woven fabric the formed media, such as felt, is placed into a corona system of about 25 Kv, slow pass, until fully charged. The resulting material holds its charge for between about 6 months to 2 years.

Operation of an Electrostatic Filter Media

In operation, a contaminated air or fluid stream is introduced to a filter employing the electrostatically charged filter media of the present invention. The air/fluid stream may be forced or drawn through the filter media by means of a pressure gradient. The stream may contain contaminant particles of various sizes to be removed or treated by the filter element. As the stream approaches the filter media, it is directed through the filter media such that the contaminate particles are brought into contact with the filter media and removed from the stream or treated by the active agent as describe elsewhere in this application. This is achieved through the properties of the filter, which causes the particles to follow a convoluted pathway through the filter element, thus increasing the time that the contaminant is in contact with the active agent. This increased contact time increases the effectiveness of the active agent in treating the particles in the stream.

The convoluted path that the particles follow is the result of the added electrostatic properties and the nonwoven properties of the substrate of the filter element. With respect to the electrostatic properties of the filter element, the convoluted pathway of the contaminant particles may be attributed to the particles polar nature. Polar molecules are neutrally charged and are also large in size. Because of the large size, the contaminants have a magnetic moment, which when subjected to an electric field causes the contaminant particle to be diverted from its pathway.

Additionally, the convoluted path of the contaminant particles is attributable to the nonwoven properties of the filter substrate. This is achieved because the nonwoven substrate had no direct and continuous pathway for the stream to pass through. Instead, due to the nonwoven properties, the substrate is made up of a porous material wherein no single pores of the material forms a continuous pathway through the substrate. Therefore, the stream and the particles carried by the stream are continuously diverted through the substrate. Accordingly, the travel time through the filter is lengthened and the exposure to the active agent is increased.

Additional Uses

The present invention can also be used in a manner consistent with existing nonwoven fabrics. Uses in various goods include both durable and disposable goods. For example, nonwovens can be used products such as diapers, feminine hygiene, adult incontinence, wipes, bed linings, automotive products, face masks, air filtration, water filtration, biological fluids filtration, home furnishings and geotextiles. The media described herein can also be used in, for example: clothing, wound dressing, air filter, shelters, and liners. Additional uses include those known in the art for electrostatic filters and antimicrobial or antitoxin filters.

In a particular embodiment, the filter media according to the present invention with or without the active agent can be used as a closure or to make a filter closure for air filters for products such as facemasks and HVAC. According to the present invention there is provided a closure material made of substrate having electrostatic properties and an electrostatic material with an active agent incorporated therein, where the material is a high loft (in one embodiment, approximately, 1" thick) breathable material of a tri-dimensional structure and is placed around the mask or air filter in order to not create a so-called airtight junction but instead creates a breathable closure that actually covers all the contours of the different geometrical surface to provided a permeable closure, having filtering properties. This approach makes the closure into a filter whereby air that bypasses the mask through gaps caused by a non-perfect fit, still passes through the closure and is filtered. In addition, contrary to a "resilient" closure the pressure differential that is detrimental in an airtight approach is reversed in our approach since the air following the path of least resistance will pass through the filter material of the mask instead. This method of closing a facemask or other filter type could also be achieved with a substitution of the non-woven filter element with a breathable foam having the same properties. Thus, while prior art facemask attempt to block air flow at the closure, the facemasks of the present invention acts as a gasket that allows air there through and kills the spores, virus, bacteria, fungi, etc. traveling through the airstream with an effective active agent, such as the iodinated resin disclosed in the '452 patent, described above. Additionally, the use of straps to hold the mask in place compresses the gasket of the present invention to fit essentially all faces.

Experimental Data

Experimental tests were performed comparing a particular embodiment of the filter media of the present invention to an existing electrostatic filter. Each test was run in the same environment to treat air with a different contaminant. The experimental data provided was collected during these tests. In each of the tests a contaminant was introduced into a chamber in a controlled amount and fed into four lines. Two of the lines included a filter according to the present invention comprising an electrostatically charged filter with an iodinated resin according the the '452 patent incorporated thereto. The third line included an electrostatically charged filter, known as Transweb. This filter does not have antimicrobial properties or any other type of active agent incorporated thereto. And a fourth line was provided as a control, having no filter and was used to confirm that the amount of contaminant entering the control chamber was equivalent to the amount of contaminant exiting the control chamber.

Exhibit A sets forth experimental data illustrating certain features of exemplary embodiments of the present invention. Experiment No. AF276, describes the performance of different filtration membranes against BG spores for 30, 60, 120, 180, 240, 300, and 360 minutes of filtration. BG spores must be present in amounts of about 8,000 to 30,000 spores to cause illness in the average human. As can be seen in Exhibit A, for each of the 30, 60, 120, 180, 240, 300 and 360-minute tests, the filter of the present invention achieved a 100% reduction of BG spores from the airstream.

As can be seen in Exhibit A, the electrostatic filter of the present invention achieves the essentially the same or similar net effect as the Transweb in these tests. However, an important advantage provided is that the present invention sterilizes the spores rather than just holding the spores to the filter. Thus, unlike the present invention, if the Transweb is handled by a user or is contacted by the skin, contamination will occur. The present invention maintains the hygiene of the filter.

Turning now to Exhibit B, the results of Experiment AF270 there is shown test results for the performance of different filtration membranes against MS2 viruses for 30, 60, 120, 180, 240 300, and 360 minutes of filtration. Virus amounts ranging from 1 to 1000 viruses will cause illness in the average human. Thus, the presence of even one virus can cause illness in a human. As can be seen in Exhibit B, for each of the 30, 60, 120, 180, 240, 300 and 360-minute tests, the filter of the present invention achieved a 100% reduction of MS2 viruses from the airstream. However, the Transweb does not achieve a 100% reduction in MS2 viruses and allows between 1000 to 10000 viral units to be found in the effluent air stream. Use of Transweb to air contaminated with MS2 viruses would not achieve desired results. Thus, as can be seen in Exhibit B, in addition to the benefits of sterilization properties described above with respect to Exhibit A, the present invention protects more effectively over viruses such as MS2 over time. Because only a small amount of viruses contaminate a human (1 to 1000 viruses), unlike the present invention, Transweb does not effectively protect a user from these viruses.

CONCLUSION

Having now described one or more exemplary embodiments of the invention, it should be apparent to those skilled in the art that the foregoing is illustrative only and not limiting, having been presented by way of example only. All the features disclosed in this specification (including any accompanying claims, abstract, and drawings) may be replaced by alternative features serving the same purpose, and equivalents or similar purpose, unless expressly stated otherwise. Therefore, numerous other embodiments of the additions and modifications thereof are contemplated as falling within the scope of the present invention as defined by the appended claims and equivalents thereto.

What is claimed is:

1. A protective media for filtering and killing microorganisms in air, said protective media comprising:
    a porous dielectric carrier;
    a biocidal active agent incorporated in or on said porous dielectric carrier, said active agent being an iodinated resin; and
    an electrostatic charge across at least a portion of said porous dielectric carrier, wherein said porous dielectric carrier is a non-woven material, and wherein said porous dielectric carrier is capable of holding an electrostatic charge in the presence of said biocidal active agent.

2. The protective media of claim 1 in which said porous dielectric carrier is a fiber based material having a fibrous matrix structure.

3. The protective media of claim 1 in which said porous dielectric carrier is a sponge like material have an open cell matrix structure, wherein the open cell matrix structure is a foam.

4. The protective media of claim 1 in which said non-woven material is a three dimensional structure configured to provide a matrix capable of physically entrapping said active agent.

5. The protective media of claim 4 in which said active agent is configured to be physically entrapped in said matrix.

6. The protective media of claim 1 in which said porous dielectric carrier comprises polymer fiber.

7. The protective media of claim 6 in which said polymer fiber comprises polypropylene.

8. The protective media of claim 6 in which said polymer fiber comprises a member selected from the group consisting of nylon, polyethylene, and polyester.

9. The protective media of claim 1 in which said porous dielectric carrier is capable of holding an electrostatic charge in the presence of said biocidal active agent for at least six months.

10. A protective media for filtering and killing microorganisms in air, said protective media comprising:
    a first porous dielectric carrier;
    a first active agent incorporated in said first porous dielectric carrier, said first active agent being a biocidal iodinated resin;
    an electrostatic charge across at least a portion of said first porous dielectric carrier;
    a second porous dielectric carrier;
    a second active agent incorporated in said second porous dielectric carrier; and
    an electrostatic charge across at least a portion of said second porous dielectric carrier, wherein each of said first porous dielectric carrier and said second porous dielectric carrier is a non-woven material, and wherein said first porous dielectric carrier is capable of holding an electrostatic charge in the presence of said biocidal iodinated resin.

11. The protective media of claim 10 in which said first active agent and said second active agent are of the same material.

12. The protective media of claim 10 in which an air gap separates said first and said second porous dielectric carriers.

13. The protective media of claim 12 in which said porous dielectric carrier is a fiber based material having a fibrous matrix structure.

14. The protective media of claim 13 in which said non-woven material is a three dimensional structure configured to provide a matrix capable of physically entrapping said active agent.

15. The protective media of claim 14 in which said active agent consists of particles configured to be physically entrapped in said matrix.

16. The protective media of claim 12 in which said porous dielectric carrier is a sponge like material have an open cell matrix structure.

17. The protective media of claim 10 in which said first porous dielectric carrier is capable of holding an electrostatic charge in the presence of said biocidal iodinated resin for at least six months.

* * * * *